United States Patent
Sotak et al.

(10) Patent No.: US 10,449,000 B2
(45) Date of Patent: Oct. 22, 2019

(54) ARCH SHAPED LASER CATHETER

(71) Applicant: THE SPECTRANETICS CORPORATION, Colorado Springs, CO (US)

(72) Inventors: Ryan Michael Sotak, Colorado Springs, CO (US); Kenneth P. Grace, Woodland Park, CO (US); Robert Lyle Carver, Colorado Springs, CO (US); George Woodrow Burton, Colorado Springs, CO (US); Brandon Thomas Hendrick, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 25 days.

(21) Appl. No.: 14/438,176

(22) PCT Filed: Oct. 24, 2013

(86) PCT No.: PCT/US2013/066609
§ 371 (c)(1),
(2) Date: Apr. 23, 2015

(87) PCT Pub. No.: WO2014/066634
PCT Pub. Date: May 1, 2014

(65) Prior Publication Data
US 2015/0289936 A1    Oct. 15, 2015

Related U.S. Application Data

(60) Provisional application No. 61/718,088, filed on Oct. 24, 2012.

(51) Int. Cl.
*A61B 18/24* (2006.01)
*A61B 18/00* (2006.01)
*A61B 18/22* (2006.01)

(52) U.S. Cl.
CPC .. *A61B 18/245* (2013.01); *A61B 2018/00345* (2013.01); *A61B 2018/00577* (2013.01);
(Continued)

(58) Field of Classification Search
CPC .................. A61B 18/245; A61B 18/24; A61B 2017/22038
(Continued)

(56) References Cited

U.S. PATENT DOCUMENTS 4,832,023 A * 5/1989 Murphy-Chutorian ...................... A61B 18/245
604/96.01
5,451,221 A * 9/1995 Cho ........................ A61B 18/24
606/14
(Continued)

FOREIGN PATENT DOCUMENTS

JP         2003135483 A    5/2003
KR    1020100138977 A    12/2010

OTHER PUBLICATIONS

International Search Report and Written Opinion issued in PCT/US2013/066609, dated Jan. 22, 2014 12 pages.

*Primary Examiner* — Daniel L Cerioni (57) ABSTRACT

Devices, methods and systems for removing unwanted tissue from within a patient's vasculature system are provided. Specifically, a laser ablation catheter having a tip with an open, arched-shaped cross section is described. The cross section of the tip enhances the catheter's ability to ablate, separate, and/or dilate the various layers within a patient's vasculature, thereby facilitating the removal undesirable lesions and fibrous tissue within a patient's vasculature.

20 Claims, 5 Drawing Sheets

(52) U.S. Cl.
CPC ............... *A61B 2018/2211* (2013.01); *A61B 2018/2238* (2013.01)

(58) Field of Classification Search
USPC .......................................................... 606/7
See application file for complete search history.

(56) References Cited

U.S. PATENT DOCUMENTS

| | | | |
|---|---|---|---|
| 5,514,128 A * | 5/1996 | Hillsman | A61B 18/245 |
| | | | 600/585 |
| 2004/0143254 A1 | 7/2004 | Vanney et al. | |
| 2004/0162548 A1* | 8/2004 | Reiser | A61B 18/24 |
| | | | 606/7 |
| 2006/0052767 A1* | 3/2006 | Weber | A61M 25/001 |
| | | | 604/523 |
| 2006/0084960 A1 | 4/2006 | Mester et al. | |
| 2010/0114081 A1 | 5/2010 | Keeler et al. | |
| 2011/0082452 A1* | 4/2011 | Melsky | A61B 18/24 |
| | | | 606/15 |

* cited by examiner

ARCH SHAPED LASER CATHETER

CROSS REFERENCE TO RELATED APPLICATIONS

The present application claims the benefit of and priority, under 35 U.S.C. § 119(e), to U.S. Provisional Application Ser. No. 61/718,088, filed Oct. 24, 2012, entitled "Laser Catheter and Lesion Models," which is hereby incorporated herein by reference in its entirety for all that it teaches and for all purposes.

FIELD OF THE DISCLOSURE

The present disclosure relates generally to devices, methods and systems for removing unwanted and/or diseased tissue, such as lesions or fibrous tissue, from a patient's vasculature system, and more specifically, to devices and techniques for separating the unwanted tissue from the healthy tissue in a patient's vasculature system using a laser ablation catheter.

BACKGROUND

Figure 1:
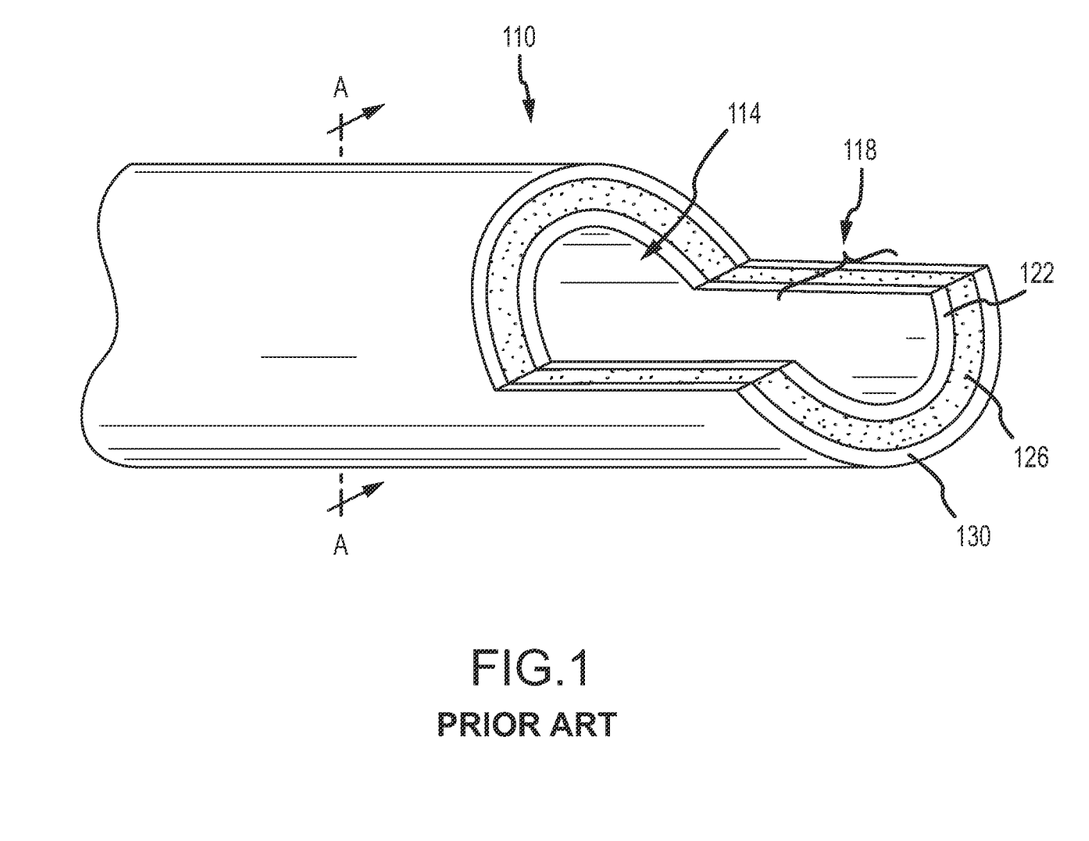
FIG. 1 shows a cut-away view of a prior art patient's vasculature.

Referring to FIG. 1, a cut-away segment of an artery 110 is shown schematically. The artery 110 includes a natural lumen 114 defined by arterial wall 118. The natural lumen 114 may also be referred to as the true lumen. The arterial wall includes multiple layers. The innermost layer of arterial wall 118 is generally referred to as the intima or intimal layer 122. Concentrically outward of the intima is the media or medial layer 126. Although the intima 122 and media 126 are each illustrated as single homogenous layers, they both typically comprise more than one layer. For the purposes of brevity and clarity within this disclosure, however, the intima 122 and media 126 are illustrated as single homogenous layers. The outermost layer of the artery is the adventitia 130. The transition between the outer portion of the intima 122 and the inner portion of the media 126 is referred to as the subintimal space. The subintimal space is sometimes referred to as a false lumen, in contrast to true lumen 114.

Figure 1A:
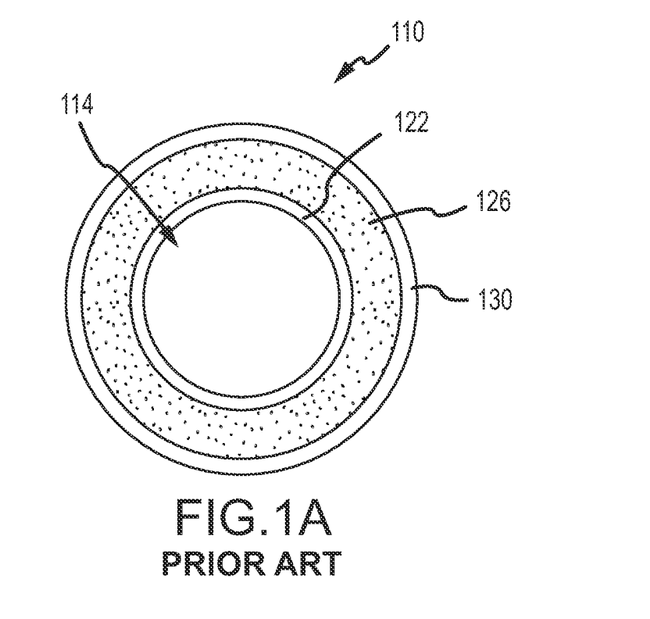
FIG. 1A shows a cross-sectional view of the prior art patient's vasculature depicted in FIG. 1 taken along line A-A.
Figure 2:
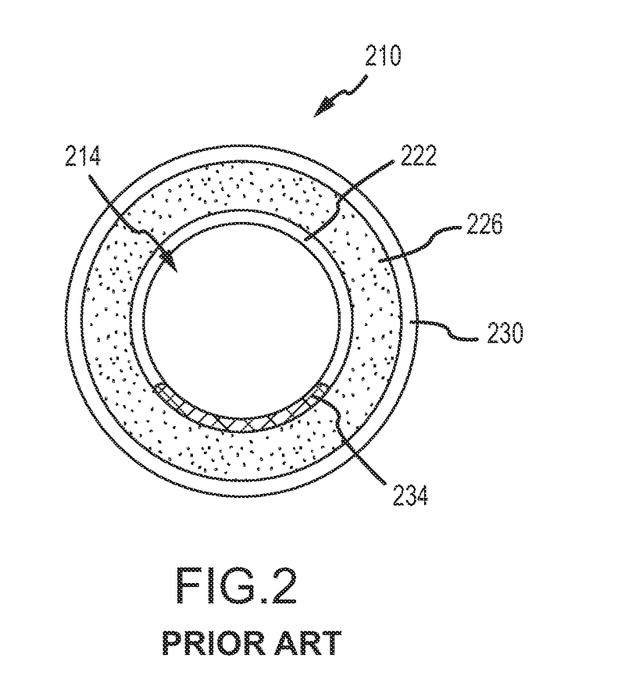
FIG. 2 shows a cross-sectional view of a prior art patient's vasculature comprising a diseased portion therein.
Figure 3:
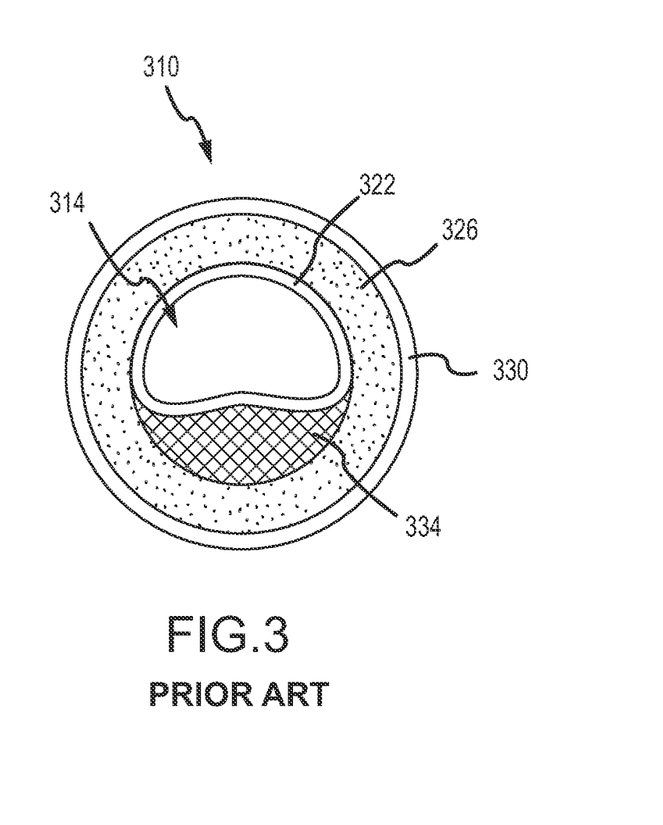
FIG. 3 shows a cross-sectional view of a prior art patient's vasculature comprising a diseased portion therein.

Referring to FIG. 1A, a cross-sectional view of the artery 110 depicted in FIG. 1 is illustrated. This artery 110 is generally healthy because it lacks any calcium deposits, plaque, calcified layers, calcified plaque, scars or other types of fibrous tissue or lesion material. FIG. 2, however, illustrates a portion 234 of the intima layer 222 that has become diseased. For example, the diseased portion 234 could be hardened, calcified and/or fibrous for a variety of health reasons. FIG. 3 illustrates calcified plaque 334 that has grown in the subintimal space between the outer portion of the intima 322 and the inner portion of the media 326. As FIG. 3 depicts, the size of the natural lumen 314 decreases as the calcified plaque 334, as well as other undesirable fibrous tissue, grows within the artery 310.

Although FIG. 2 and FIG. 3 only illustrate disease states, such as calcification, plaque and/or other types of fibrous tissue or lesion material in the intima layer 222 and the subintimal space, these disease states may form in other areas of the vasculature, such as the media 226, 326. Additionally, the inner portion of the intima layer may burst and obstructions may form within the natural lumen 214, 314. Accordingly, there is a need for a device, method and/or system that has the ability to remove the diseased portions of a patient's vascular system.

SUMMARY

The present disclosure describes a catheter comprising a shaft having a proximal end and a distal end, a tip coupled to the distal end of the shaft, wherein the tip comprises an open arch-shaped cross sectional profile taken along a plane perpendicular to a longitudinal axis of the tip and/or shaft, and a plurality of optical fibers having an exposed end, wherein the optical fibers are encapsulated within the shaft and the tip, and wherein the exposed end of the optical fiber is exposed at the tip.

Additionally, the arch-shaped tip includes both an inner exterior surface and an outer exterior surface. Either or both of the exterior surfaces can, in turn, have arcuate shapes as they progress from the proximal end of the tip to the distal end of the tip. The inner and outer shaped arcuate-shaped surfaces of the tip may or may not be parallel, may or may not have a common radius, may or may not subtend a common angle, and may or may not have a common length.

The tip's open, arch-shaped cross-sectional profile—either alone or in combination with the tip's inner and/or outer arcuate-shaped surface(s)—enhances the catheter's ability to separate and remove unwanted lesions or fibrous tissue within a patient's vasculature. The catheter, particularly the tip, may enter the vasculature through an incision and between the vascular layers. The tip emits laser energy in a pattern determined by the tip's cross-sectional profile. For instance, the emitted laser energy will be in an open arch-shaped cross sectional profile taken along the same plane as the cross sectional profile of the tip. Upon the shaft of the catheter being pushed along between the vascular layers, the laser energy emitted by the optical fibers at the tip of the catheter ablates, separates, and/or dilates the intersection of such layers, wherein at least one of these layers includes the diseased tissue. Once the tip of the catheter passes the diseased portion, the tip—due in part to its inner and/or outer shaped arcuate-shaped surface(s)—naturally moves radially inward and enters the vascular lumen, thereby allowing the surgeon to remove the dissected and unwanted lesion and/or tissue. Accordingly, the open, arch-shaped tip not only acts as an ablation tool, but it also acts as a scoop-like separator and/or dilator to facilitate the removal of the unwanted tissue within a patient's vasculature, particularly when the tip's inner and/or outer surface(s) have an arcuate-shape.

In another aspect of the present disclosure, the configuration and/or arrangement of the optical fibers in the tip may create different optical fiber densities at differing locations around the tip. For instance, a first location of the tip may have a first optical fiber density, and a second location of the tip may have a second optical fiber density that is different than the first optical fiber density. That is, the first tip location may have a plurality of optical fibers while the second tip location may have one optical fiber. Additionally, a third tip location may have no optical fibers, such as the open portion of the tip where the optical fiber density is zero.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "arc" shall mean a continuous portion of the circumference of a circle or other curved line.

The term "arch" shall mean the shape of an object bowed or curved in a particular direction.

The term "arcuate" shall mean shaped like a bow or curved.

The term "crescent" shall mean the shape of an object that is broad in the center and tapered at each end.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "open arch" shall mean an arch that is less than 360 degrees concentrically (e.g., subtends an angle of less than 360 degrees). That is, the arch is not closed, as it would be in a circle or ellipse.

The term "subtended angle" shall mean an angle subtended by an arc, line, or other curve is one whose two rays pass through the endpoints of the arc.

The term "vasculature" shall mean blood vessels, such as veins and arteries, in the body or in an organ or body part. Although portions of this disclosure may refer to veins and arteries, this disclosure shall be applicable to any type of blood vessel within the "vascular system."

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 4:
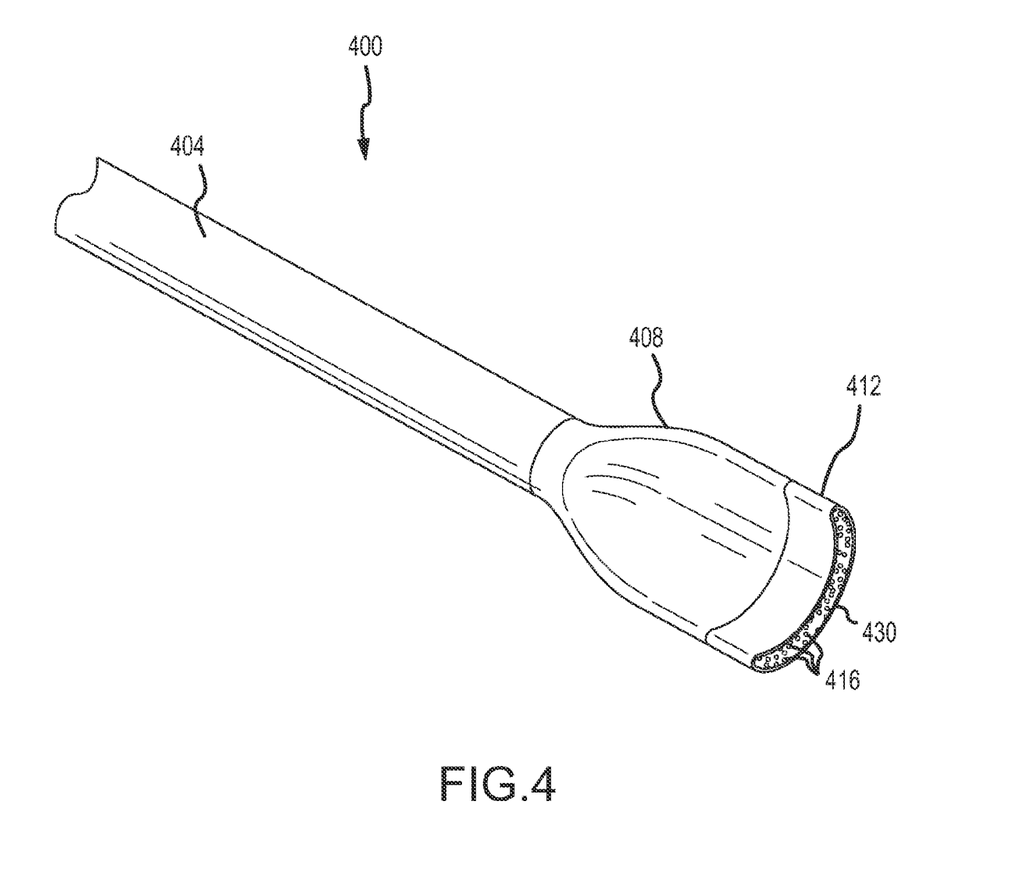
FIG. 4 shows a perspective view of a catheter in accordance with embodiments of the present disclosure.

FIG. 4 depicts an exemplary catheter 400 in accordance with embodiments of the present disclosure. Catheter 400 includes a shaft 404 and a tip 412. The shaft 404 includes a proximal end and a distal end, wherein the proximal end of the shaft 404 is coupled to a laser source (not shown), and the distal end is coupled to the tip 412.

The shaft 404 may by solid or hollow. Referring to FIG. 4C, if the shaft 404 is hollow, it will include an inner lumen 436 that typically runs from its proximal end toward the distal end. The lumen may be used in a way to allow a guide wire, a mandrel (discussed below), an infusion material and/or other objects or materials to be inserted or injected. Also, although not depicted in FIG. 4B, the shaft 404 may include more than one lumen. As illustrated in this figure, the shaft may have a circular cross sectional shape. Additionally, although not illustrated, the shaft may have a non-circular shape, such as an oval, rectangular, square, triangular, etc. or any combination thereof.

Regardless of whether the shaft is solid or hollow, it may be constructed of a bio-compatible plastic reinforced with a metal structure, such as a braid, to increase the stiffness of the shaft. A solid shaft is generally stiffer than a hollow shaft. Accordingly, when using a hollow shaft, it may be desirable to also use a mandrel that fits within the inner lumen of the shaft, thereby increasing the stiffness and potential control of the shaft. There are various types of mandrels known in the art. One such mandrel includes a tapered configuration that provides the shaft with a variable stiffness at the mandrel moves along the length of the inner lumen.

As depicted in FIG. 4, the distal end of the shaft 404 is coupled to the tip 412 by a tapered portion 408. The tapered portion 408 may be integral with the shaft 404, may be integral with the tip 412, or may be a separate component the couples the shaft 404 and the tip 412. As will become evident below, one of the purposes of the tapered portion 408 is to transition from the shaft 404 to the tip 412, which in turn has an arch-shaped cross-sectional configuration.

The tapered portion 408 has inner and outer sides and/or exterior surfaces. The width of the inner and outer exterior surfaces may be smaller at and/or proximally toward the shaft 404 in comparison to tip 412. That is, the inner and outer exterior surfaces of the tapered portion 408 may be greater at and/or distally toward tip 412 in comparison to the shaft 404. The profile of the inner and outer exterior surfaces of tapered portion 408 may be linear or non-linear (e.g., curvilinear) as they transition from the shaft 404 to the tip 412. One example of a curvilinear shaped surface is an arcuate-shaped surface. Specifically, the inner exterior surface may be curved inwardly to create a concave-type shape, and the outer exterior surface may be curved outwardly to create a convex-type shape.

The combination of the concave-shaped inner exterior surface and the convex-shape outer exterior surface creates a scoop-like structure, which enhances the tapered portion's and catheter's ability to separate and remove unwanted lesions or fibrous tissue within a patient's vasculature. Although the inner (e.g., concave) and outer (e.g., convex) surfaces may be parallel to one another, may have a common radius, may subtend to a common angle, and may have a common length they also may not.

In transitioning from the shaft 404 to the tip 412, the tapered portion 408 may include one or more inner lumen (not shown) that cooperates with the inner lumen 436 of the shaft 404. Similarly, the tip 412 may also include one or more lumen (not shown) that cooperates with the lumen(s) of the shaft 404 and/or tapered portion 408. Accordingly, a guide wire, a mandrel, an infusion material and/or other objects or materials to be delivered from the proximal end of the shaft 404, through the tapered portion 408, and to the distal end of the tip 412.

As discussed above, the shaft 404 may have a circular (360 degree) cross-sectional profile, and the tip may have an open, arch-shaped cross-sectional profile, wherein the arc is less than 360 degrees. The tip 412 may be constructed of a bio-compatible metal, and potentially in the shape of a metal band. The metal provides the catheter 400 with strength and durability, particularly at its most distal end. Due at least in part to the metallic nature of the tip 412, it may also be preferable for the ends 420, 424 of the tip 412 to be rounded and polished.

Similar to the tapered portion 408, the tip 412 may have an inner side and/or surface 428 and an outer side and/or surface 432. The profile of the inner exterior surface 428 and outer exterior surface 432 of tip 412 may be linear or non-linear as they transition proximally to distally. As discussed above with respect to the tapered portion 408, an example of a non-linear shaped surface is an arcuate-shaped surface. Therefore, the inner exterior surface 428 may be curved inwardly to create a concave-type shape, and the outer exterior surface 432 may be curved outwardly to create a convex-type shape. The combination of the concave-shaped inner exterior surface 428 and the convex-shaped outer exterior surface 432 creates a scoop-like structure, which enhances the tip's and catheter's ability to separate and remove diseased tissue within a patient's vasculature. It will also be appreciated by those of skill in the art that the scoop-like structure of the tapered portion 408 and the scoop-like structure of the tip 412 can be coordinated to create a larger scoop-like structure when the tapered portion 408 and the tip 412 are coupled. Namely, the inner and outer exterior surfaces of the tapered portion 408 and the inner and outer exterior surfaces of the tip 412 may follow a similar non-linear (i.e., curved) trajectory when adjacent one another, particularly when the distal ends of the inner and outer exterior surfaces of the tapered portion 408 abut or approximate the proximal ends of the inner and outer exterior surfaces of the tip 412.

The catheter 400 will be used within a patient's vasculature, which typically includes blood vessels having a diameter of up to 8 millimeters. Accordingly, the width of the catheter 400 is designed to fit within such blood vessels and may likely have an overall width of less than 8 millimeters. The width of the shaft 404, tapered portion 208, and the tip 412 may be the same or different. For example, as depicted in FIG. 4, it may be desirable for the cross section of the tip 412 to be larger than the cross section of the shaft 404. If so, the tapered portion 408 transitions from a smaller cross section to a larger cross section viewed from the perspective of the proximal to the distal end of the catheter. Although it is not depicted in the figures, it may be desirable for the cross section of the tip 412 to be smaller than the cross section of the shaft 404. If so, the tapered portion would transition from a larger cross section to a smaller cross section viewed from the perspective of the proximal to the distal end of the catheter.

Figure 4A:
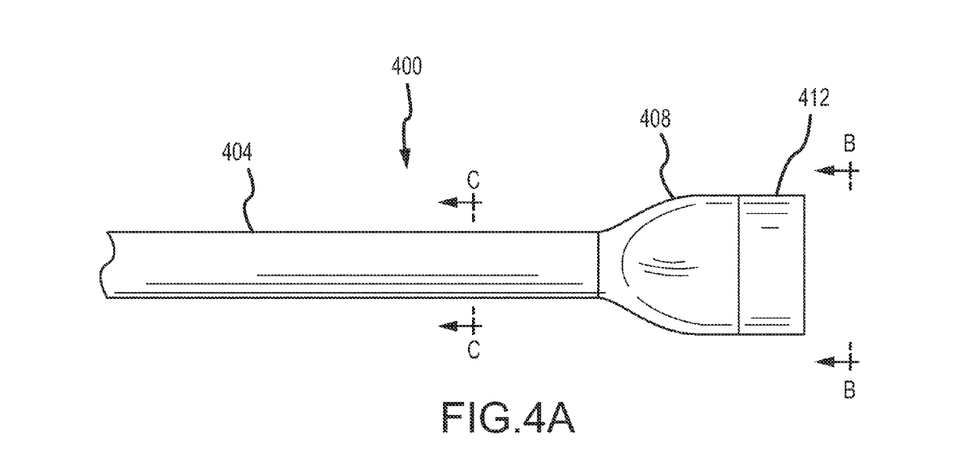
FIG. 4A shows a top view of a catheter illustrated in FIG. 4.

Referring to FIG. 4A, the distal end of the tip 412 is depicted as linear. That is, the distal end of the tip 412 is illustrated as flat. However, the distal end of the tip 412 may be curvilinear. For example, the ends 420, 424 of the tip 412 may be radially curved from the distal end of the tip 412 toward the proximal end of the tip 412.

Figure 4B:
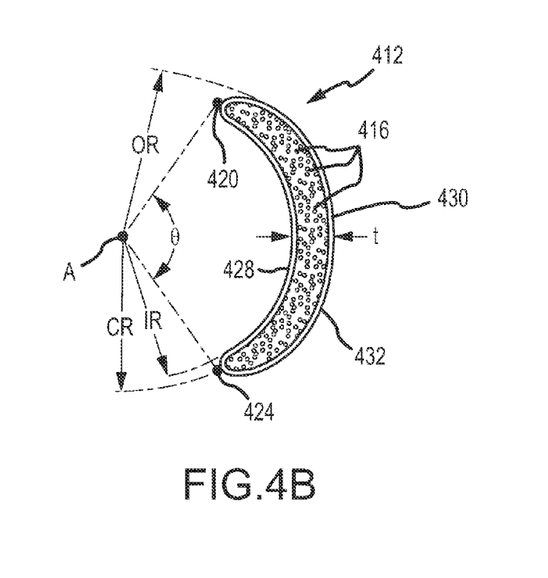
FIG. 4B shows an end view of the tip of the catheter illustrated in FIG. 4A taken along line B-B.
Figure 4C:
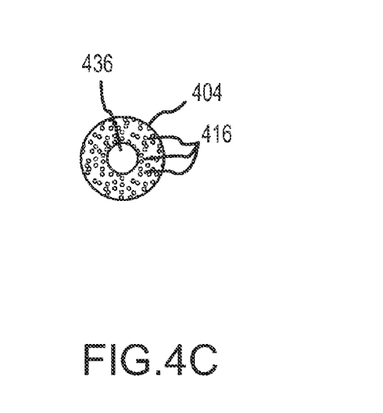
FIG. 4C shows an end view of the shaft of the catheter illustrated in FIG. 4A taken along line C-C.

As depicted in FIGS. 4B and 4C, the optical fibers 416 are embedded within the shaft 404 and the tip 412. If the catheter 404 includes a tapered portion 408, the optical fibers 416 will also be embedded therein. The proximal ends of the optical fibers become attached to the laser generator when the proximal end of the catheter is coupled to a laser. As depicted in FIG. 4B, the distal ends of the optical fibers 416 are exposed at the distal end of the tip 412. The overall length of the catheter 400 is dependent upon the procedure for which the catheter 400 will be used, but it may be desirable for the catheter to have a length of up to 45 centimeters. Accordingly the optical fibers 416 will have a similar length.

FIG. 4B depicts multiple rows of optical fibers 416 embedded within the tip 412. The tip 412, however, may only have one row of optical fibers 416. The configuration and/or arrangement of the optical fibers in the tip 412 may also create different optical fiber densities at differing locations of the tip. For example, the optical fibers may have different sizes such that some optical fibers are larger at one location within the tip 412 in comparison to smaller sized optical fibers at a different location within the tip 412. An additional example includes a first location of the tip having a first optical fiber density, and a second location of the tip having a second optical fiber density that is different than the first optical fiber density. For instance, the first tip location may have a certain number of optical fibers while the second tip location may have a reduced number optical fibers.

The cross-sectional profile of the tip 412 taken along a plane perpendicular to a longitudinal axis of the tip and/or the shaft, particularly the distal portion of the tip, has an open, arch-shaped cross section. The open, arch-shaped cross section may include a variety of different profiles. One such cross sectional profile may be referred to as a crescent-shaped cross sectional profile, which is depicted in FIG. 4B. The distal end of the tip 412 has an inner side and/or surface 428, an outer side and/or surface 432, and two rounded ends 420, 424. The thickness (t) of the tip 412 may be constant or vary at different locations. For example, the crescent-shaped cross sectional profile depicted in FIG. 4B has a greater thickness (t) at its central region 430 in comparison to the thickness (t) at its ends 420, 424. For example, if the thickness (t) of the tip 412 at the central region 430 is about 1 millimeter to 2 millimeters, and possibly 1 millimeter to 1.5 millimeters, and possibly about 1.2 millimeters, the thickness (t) of the tip 412 will be less than such dimensions toward the ends 420, 424. However, it shall be understood that the cross-sectional profile of the tip 412 may be generally similar such that the thickness of the tip is the same at the central region 430 and at (or toward) both ends 420, 424.

Continuing to refer to FIG. 4B, the outer side and/or surface 432 of the tip 412 has an outside radius (OR) measured from an imaginary point A, and the inner side and/or surface 428 of the tip 412 has an inner radius (IR) measured from imaginary point A. The tip 412 also has a central radius (CR) measured from imaginary point A to the center of the tip 412. It may be preferable for the inner radius (IR), central radius (CR), and/or outside radius (OR) to be constant and/or variable when such radii are measured from imaginary point A as the radii move from one end 420 to the other end 424, or vice versa, of the tip 412. For example, it may be desirable for the inner radius (IR) to be constant while the outer radius (OR) is variable. Alternatively, it may be desirable for the inner radius (IR) to be variable while the outer radius (OR) is constant. A further alternative may include both the inner radius (IR) and the outer radius (OR) being constant or variable.

With further reference to FIG. 4B, not only may the thickness (t), inner radius (IR), and outer radius (OR) of the tip 412 affect the arch-shaped cross sectional profile of the tip 412, so may the subtended angle (θ) of the arc, which is viewed from imaginary point A to both ends 420, 424 of the tip 412. It is generally preferable that the subtended angle (θ) be greater than zero degrees and less than 360 degrees. It may also be preferable for the subtended angle (θ) to be greater than, less than or equal 180 degrees. Assuming the subtended angle (θ) is less than 180 degrees, it may be preferable that the subtended angle (θ) be greater than 90 degrees and less than 150 degrees, and it may be even more preferable that the subtended angle (θ) be greater than 100 degrees and less than 140 degrees, and it may be even further preferable that the subtended angle (θ) be greater than 110 degrees and less than 130 degrees, and possibly preferable that the subtended angle (θ) be about 120 degrees. As mentioned above, it is generally preferable that the subtended angle (θ) be greater than zero degrees and less than 360 degrees; hence, the subtended angle (θ) may be about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350 or 355 degrees. The arc length of the tip 412 is dependent upon the angle (θ). Accordingly, the arc length of tip 412 will be equal to about $$2\pi(CR) * \frac{\theta}{360},$$

wherein CR is the central radius.

Having a tip 412 with an open, arch-shaped cross-sectional profile, and potentially a non-circular arch-shaped cross-sectional profile having a variable inner radius (IR), outer radius (OR), thickness (t), and/or angle (θ), enhances the catheter's ability to separate and remove unwanted lesions within a patient's vasculature. As discussed above, the cross-sectional arch-shape of the tip 412 is dependent upon the tip's inner radius (IR), outer radius (OR), thickness (t), and angle (θ). The possible combinations of these variables, and potentially others, allows the cross section of the tip 412 to take on numerous shapes. And either alone or in conjunction with the tapered portion 408, the tip 412 creates a scoop-like structure capable of emitting laser energy in accordance with the tip's cross-sectional profile, thereby acting as an ablation tool, separator and/or dilator to facilitate the removal of the unwanted tissue within a patient's vasculature.

For example, as discussed above with respect to FIG. 2, a portion 234 of the intima layer 222 may be diseased, and a surgeon (along with a patient's permission) may wish to remove the diseased portion. To remove the diseased portion 234, the surgeon may create an incision in the patient's tissue to reach the patient's vasculature. Once the vasculature is reached, the surgeon will transversely cut the vasculature, thereby exposing its multiple layers. Thereafter, the surgeon may insert the tip 412 of the catheter 400 at the incision into the vasculature, particularly between the intima 222 and the media 226 where the diseased portion 234 exists. The laser energy is transferred from the laser source (not shown) through the catheter 400 to the tip 412 via the optical fibers 416. As the surgeon continues to push the shaft 404 of the catheter 400 along this intersection of the vascular layers, the laser energy emitted by the optical fibers 416 at the tip 410 of the catheter 400 ablates, separates, and/or dilates the intersection of the intima 222 and the media 226. Once the tip passes the calcified portion 234, the tip 412 of the catheter 400 naturally enters the lumen 214 of the vasculature, and the surgeon can then remove the dissected and unwanted lesion and/or tissue.

The configuration and shape of the tip 412, particularly its open, arched-shaped configuration, facilitates and enhances the catheter's ability to ablate, separate, and/or dilate the different vascular layers, as well as the intersection of such layers that include diseased portion(s) or undesirable fibrous tissue. The tip's inner and/or outer arcuate-shaped exterior surface(s) may further enhance the catheter's ability to traverse the patient's vasculature due to its scoop-like nature. Moreover, the addition of the tapered portion 408 and particularly the addition of a concave-shaped inner exterior surface 428 and/or the convex-shape outer exterior surface 432 may also increase the scooping capability of the catheter 400.

Another example of using such a catheter 400 is in reference to FIG. 3, wherein the tip 412 can enter the vasculature and ablate and/or dilate the calcified plaque 334 that has grown in the subintimal space between the outer portion of the intima 322 and the inner portion of the media 326. Additionally, if the vasculature contains a lesion and/or undesirable fibrous tissue within the media, the tip 412 can remove the fibrous tissue by ablating, separating, and/or dilating the intersection between the outer portion of the media and the inner portion of the adventitia. Furthermore, the catheter 400 and open, arch-shaped tip 412 may be used to remove lesions and/or undesirable fibrous tissue within a patient's vasculature by ablating the layers and intersection between the layers in such vasculature.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

A number of variations and modifications of the disclosure can be used. It would be possible to provide for some features of the disclosure without providing others. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation. Additionally, those of skill in the art will understand how to make and use the disclosed aspects, embodiments, and/or configurations after understanding the present disclosure. By way of example, in addition to using the catheter described in the present disclosure to remove unwanted diseased tissue, such as lesions or fibrous tissue, from a patient's vasculature system, the catheter may also be used to remove implanted objects, such as stents, filters, shunts, and leads (e.g., defibrillator leads and pacemaker leads) from a patient's vasculature system. Furthermore, as discussed above, the surgeon can access the patient's vasculature in a non-invasive (or minimally invasive) manner and insert the tip 412 of the catheter 400 into the vasculature in situ. The catheter 400 can also be used in a similar manner but in an invasive surgical procedure, such as open surgery.

The foregoing discussion has been presented for purposes of illustration and description. The foregoing is not intended to limit the disclosure to the faun or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Summary, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A catheter comprising:
a shaft having a first proximal end, a first distal end, and a longitudinal axis;
a tapered portion coupled to the distal end of the shaft, the tapered portion comprising a second proximal end, a second distal end, an inner exterior surface, and an outer exterior surface, wherein widths of the inner exterior surface and the outer exterior surface increase proceeding from the second proximal end to the second distal end;
a tip fixed to the second distal end of the tapered portion, wherein the tip comprises a distal portion comprising an open arch-shaped cross sectional profile taken along a plane perpendicular to the longitudinal axis, wherein the plane is viewed from a point distal to the distal portion, and wherein the distal portion comprises a third proximal end and a third distal end, and a surface comprising a length between the third proximal end and the third distal end, wherein the length of the surface comprises the open arch-shaped cross sectional profile having a predetermined radius, is parallel to the longitudinal axis and is at least partially constructed of metal, and
a plurality of optical fibers each having an exposed end at the distal portion, wherein at least one of the plurality of optical fibers is encapsulated within the shaft, the tapered portion and the tip, and wherein the exposed end of the at least one of the plurality of optical fibers is coplanar with the plane.

2. The catheter of claim 1, wherein the arch-shaped cross sectional profile comprises a center portion and two ends.

3. The catheter of claim 2, wherein at least one of the ends of the arch-shaped cross sectional profile is rounded.

4. The catheter of claim 2, wherein the arch-shaped cross sectional profile is crescent shaped.

5. The catheter of claim 2, wherein the center portion of the arch-shaped cross sectional profile is approximately the same as one of the ends.

6. The catheter of claim 2, wherein the arch-shaped cross sectional profile has an angle ($\theta$) created by a radial intersection of radii from the two ends.

7. The catheter of claim 6, wherein the angle ($\theta$) is greater than 0 degrees and less than 360 degrees.

8. The catheter of claim 7, wherein the angle ($\theta$) is greater than 110 degrees and less than 130 degrees.

9. The catheter of claim 6, wherein the angle ($\theta$) is about 120 degrees.

10. The catheter of claim 1, wherein the arch-shaped cross sectional profile has an inner radius and an outer radius, and the inner radius comprises the predetermined angle.

11. The catheter of claim 10, wherein the inner radius is substantially fixed.

12. The catheter of claim 11, wherein the outer radius is variable.

13. The catheter of claim 10, wherein the outer radius is substantially fixed.

14. The catheter of claim 13, wherein the radius is variable.

15. The catheter of claim 10, wherein the arch-shaped cross sectional profile has an inner radius and an outer radius and wherein at least one of the inner radius and the outer radius is variable.

16. The catheter of claim 1, wherein the shaft is hollow having a lumen running from the proximal end.

17. The catheter of claim 1, wherein the shaft is substantially solid.

18. The catheter of claim 1, wherein the outer exterior surface is curvilinear from the second proximal end to the second distal end.

19. The catheter of claim 18, wherein the inner exterior surface is curvilinear from the second proximal end to the second distal end.

20. The catheter of claim 19, wherein the inner exterior surface comprises a concave-type shape and the outer exterior surface comprises a convex-type shape, thereby creating a scoop-like structure.

* * * * *